United States Patent [19]

Harwich

[11] Patent Number: 5,398,642
[45] Date of Patent: Mar. 21, 1995

[54] OBSERVATION AND FEEDING DEVICE FOR CRAWLING INSECTS, PARTICULARLY ANTS

[76] Inventor: Mary B. Harwich, P.O. Box 533, Glencoe, Ill. 60022

[21] Appl. No.: 79,464

[22] Filed: Jun. 18, 1993

[51] Int. Cl.$^6$ ............................................. A01K 67/04
[52] U.S. Cl. ............................................. 119/6.5; 43/121
[58] Field of Search ........... 119/6.5, 6.6, 15, 246, 119/253; 43/107, 121, 122

[56] References Cited

U.S. PATENT DOCUMENTS

| | | | |
|---|---|---|---|
| 948,805 | 2/1910 | Akerlund | 119/6.5 |
| 1,092,314 | 4/1914 | White . | |
| 1,312,573 | 8/1919 | Pichat | 43/107 |
| 2,267,883 | 12/1941 | Wood . | |
| 2,845,895 | 8/1958 | Balkauskas . | |
| 2,931,336 | 4/1960 | Cather . | |
| 3,244,150 | 4/1966 | Blair . | |
| 3,260,236 | 7/1966 | Jones | 119/15 |
| 3,269,578 | 8/1966 | Lewis | 119/246 |
| 3,399,650 | 9/1968 | Goodman . | |
| 3,653,357 | 4/1972 | Sheidlower | 119/15 |
| 3,687,110 | 8/1972 | Braunhut | 119/15 |
| 3,948,220 | 4/1976 | Fiedler . | |
| 4,117,805 | 10/1978 | Ward | 119/246 |
| 4,250,833 | 2/1981 | Waldon | 119/15 |
| 4,351,270 | 9/1982 | Salin | 119/246 |
| 4,434,745 | 3/1984 | Perkins et al. . | |
| 4,441,272 | 4/1984 | Bartz . | |

FOREIGN PATENT DOCUMENTS

| | | | |
|---|---|---|---|
| 187952 | 12/1936 | France . | |
| 0468155 | 6/1937 | United Kingdom | 119/6.5 |
| 1230567 | 5/1986 | U.S.S.R. | 119/6.5 |

*Primary Examiner*—P. Austin Bradley
*Assistant Examiner*—James Miner
*Attorney, Agent, or Firm*—Lockwood, Alex, FitzGibbon & Cummings

[57] ABSTRACT

An insect observation and feeding device which is particularly suitable for ants has a central core member contained within a protective outer enclosure. The central core member extends within the enclosure between a base portion and an entrance portion and includes one or more predetermined surfaces which may define a plurality of distinct levels. Some of the levels may be used for the support of food while other levels may include members for enhancing insect observation, such as structures that require the insects to move across different terrain, including ladder-like devices, maze patterns and the like.

12 Claims, 2 Drawing Sheets

U.S. Patent   Mar. 21, 1995   Sheet 1 of 2   5,398,642
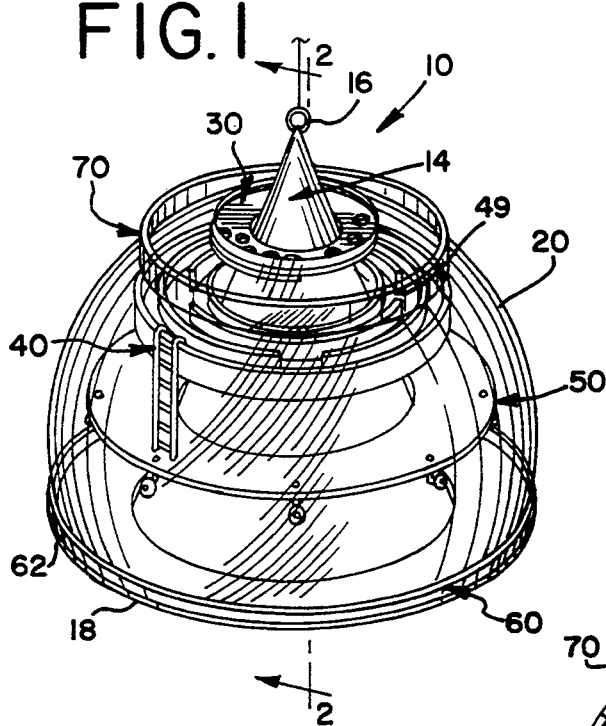
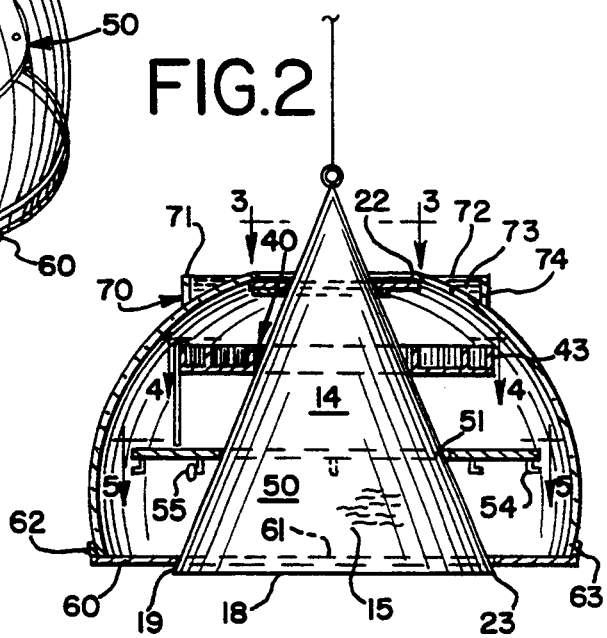
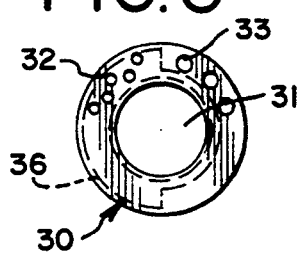
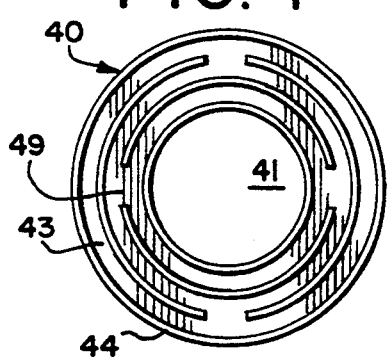
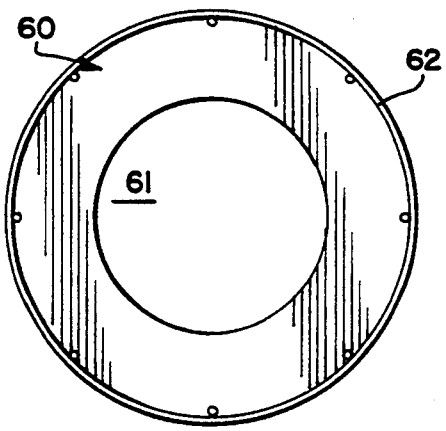

OBSERVATION AND FEEDING DEVICE FOR CRAWLING INSECTS, PARTICULARLY ANTS

BACKGROUND AND SUMMARY OF THE INVENTION

The present invention relates generally to an apparatus which permits one to feed and observe insects, and more particularly, to an ant feeding and observation apparatus.

Certain structures are known for the observation of crawling insects, such as ants. These structures are commonly referred to as "ant farms"0 and typically contain a particulate media, such as sand or earth, which is held between two parallel sidewalls through which the ants tunnel. These type of devices must be displayed in a horizontal orientation and present the nature of ants for observation under "captive" conditions. However, such devices are not adaptable for outdoor use because when water enters the space between the sidewalls, swelling and expansion of the media may result.

The present invention is directed to an apparatus which permits feeding and observation of crawling insects, such as ants, in a natural state, and which apparatus has a simplified structure and which can be used outside without a problem in dry or wet conditions.

Accordingly, it is an object of the present invention to provide an insect feeding and observation apparatus which is particularly suitable for the feeding and observing of ants having a relatively simple construction and having protection against the elements and some measure of protection against larger, predatory animals and insects.

Another object of the present invention is to provide an ant feeding and observation device having multiple levels for transit by the ants, the levels being positioned within a protective enclosure such that viewing of the ants on each level is possible.

Yet another object of the present invention is to provide an ant feeder having multiple levels of transit for ants, at least one of the levels having a labyrinth portion and another of the levels having a feeding portion.

Still another object of the present invention is to provide an ant observation and feeding apparatus having multiple, separate levels positioned within an enclosure and which permits observation of ants on all levels in a natural state, the enclosure providing protection from birds and other similar animals from entering the apparatus.

These and other objects of the present invention are provided by a central support or core member which extends vertically within a enclosure member, such as a globe or cylinder, and which supports various levels or platforms of the apparatus. The core member includes multiple horizontal members which are spaced apart within the enclosure and which provide distinct observation and/or feeding levels for the apparatus. The levels may have a maze or labyrinth pattern imposed thereon which retards movement of the ants from one level to the next and which permits extended observation of the ants on a specific level. Such an apparatus allows one to observe the feeding and movement of insects in a "natural" state rather than in a "captive" state.

These and other objects, features and advantages of the present invention will become apparent from the following detailed description of the preferred embodiments of this invention taken in conjunction with the accompanying drawings.

BRIEF DESCRIPTION OF THE DRAWINGS

FIG. 1 is a perspective view of an embodiment of an insect observation and feeding apparatus constructed in accordance with the present invention;

FIG. 2 is a partial sectional view generally taken along line 2—2 of FIG. 1;

FIG. 3 is a partial sectional view taken along line 3—3 of FIG. 2 showing the entrance level;

FIG. 4 is a partial sectional view taken along line 4—4 of FIG. 2 showing an intermediate labyrinth level; and FIG. 5 is a partial sectional view taken along line 5—5 of FIG. 2 showing an intermediate feeding level;

DESCRIPTION OF THE PREFERRED EMBODIMENTS

Figure 6:
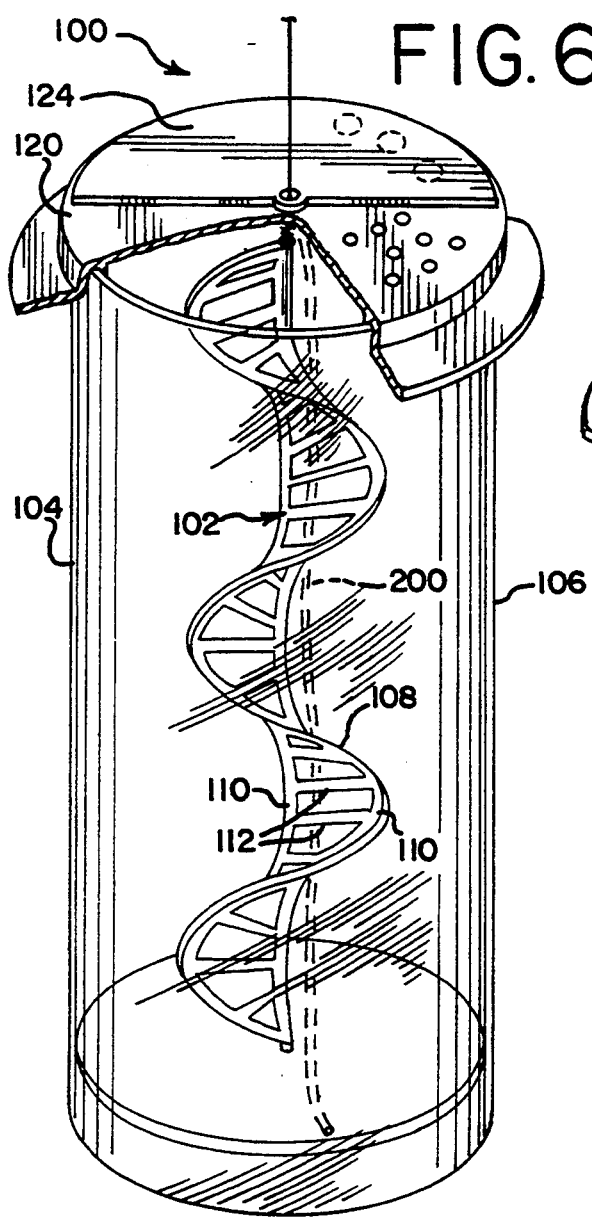
FIG. 6 is a perspective view of an alternative embodiment of an insect feeding and observation apparatus constructed in accordance with the principles of the present invention.
Figure 8:
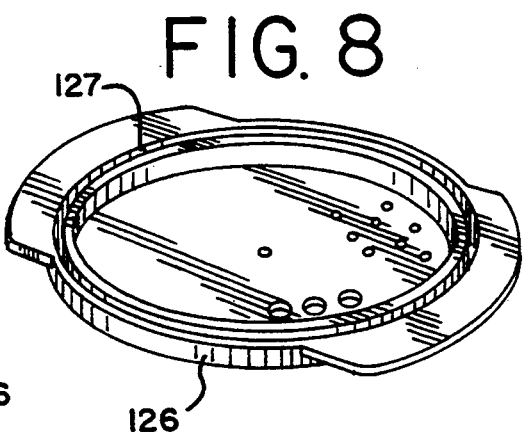
FIG. 8 is a perspective view of a water barrier ring used in association with the apparatus of FIG. 6; and, FIG. 9 is a perspective view of an other alternative construction of a core member suitable for use in an apparatus as generally shown in FIG. 6.

Turning now to the drawings, FIGS. 1-5 illustrate a first embodiment of an insect feeding and observation apparatus, generally designed as 10, constructed in accordance with the principles of the present invention. Although the structure and operation of the feeding and observation apparatus will be described in the detailed description which follows in terms of the feeding and observation of ants, it will be appreciated that the present invention will provide substantially equal advantages to the feeding and observation of other insects.

Apparatus 10 includes a central core or support member, such as illustrated cone 14 which provides a vertical support surface for a plurality of horizontal members 30, 40, 50 and 60. The core member preferably has a ring 16, or other similar means, suitably located such at its apex as shown, by which the apparatus 10 may be hung outside from a tree or post for example, by way of a string or wire. The base 18 of the core member 14 is preferably level so that it may provide a support for the apparatus in situations where the apparatus is intended to be supported from below such as resting on the ground rather than hung from a standing structure.

The core member base 18 may have a rim member 19 attached thereto and extending around the lower periphery thereof. The core member 14 includes an exterior surface 15 which may be textured in a manner which permits the attachment of food thereto such as the serrations illustrated, and the passage of ants thereupon from one level to the next. Core member 14 may be transparent, translucent or opaque.

With further reference to the plurality of horizontal members 30, 40, 50 and 60, they are vertically spaced apart at preselected distances along the cone 14. These members define distinct levels within an enclosure 20 and may be considered as individual platforms, with each platform preferably serving a purpose different from the functions of the other platforms.

Enclosure 20 protectively encloses the central core member 14 and its associated platforms 30, 40, 50 and 60 in a manner such that the platforms are readily visible through the enclosure 20. As shown in FIGS. 1–5, the enclosure 20 may take a form resembling that of a globe, such as the truncated sphere which is illustrated. Enclosure 20 has a pair of openings 22, 23 disposed on opposite ends to accommodate the core member 14. Enclosure 20 serves as a protective barrier against larger animals and insects which may feed on ants. Preferably, the entirety of the enclosure is formed from a transparent material such as glass or plastic which permits unobstructed observation of the interior components when the device is viewed from the outside, although the enclosure could be transparent at a selected location or locations and opaque at another selected location or locations.

Working downwardly from the top of the apparatus 10, the first interior level or platform 30 is shown positioned near the top opening 22 of the globe 20. This first platform 30 serves as an entryway into the apparatus 10 for the insects. The platform 30 is formed with a central opening 31 having a diameter equivalent to the diameter of the cone 14 at a preselected height or level on the cone. The platform 30 is provided with a series of holes or openings 32 and 33, disposed in a portion of the platform 30, shown illustrated as extending in a general semicircular pattern. The platform 30 has a width or outer diameter which is greater than the diameter of the enclosure 20 at this location. This permits an annular rim 34 of the platform to abut the inner rim 24 of the enclosure in a supporting manner.

Two differently sized openings 32, 33 are preferably provided in the first platform 30, which openings permit the selective entrance to or exit from the enclosed device of small ants or large ants. For smaller ants, openings 32 should preferably have a diameter of approximately 1/16 inch (1.5–2 mm), and for larger ants, the openings 33 should preferably have a diameter of approximately ¼ to 178 inch (6–12 mm).

The top plate 30 may also include a closure plate 36 associated therewith which has a configuration such that it selectively covers the openings 32 of this plate or platform 30. The closure plate 36 is illustrated as having a semi-circular shape (located beneath the top plate) and may be rotated around its axis to selectively close off either the small openings 32 or the large openings 33, or both.

Disposed beneath the first platform or top plate 30 is a second level or platform 40 which also has a circular opening 41 centrally disposed therein. The diameter of the second platform opening 41 is greater than that of the first platform opening 31 so that it engages the cone 14 at a different level and apart from that of the first plate 30 in a spaced-apart relationship therefrom. The second plate 40 is primarily provided for observation purposes of the ants and, as such, may contain a labyrinth or maze thereon 43 comprised of a plurality of upstanding walls 44. Walls 44 preferably include gaps 49 therealong through which the ants may crawl to move from a ring defined by walls 44 to an adjoining ring. The maze 43 presents the ants with a diversion to permit extended observation of the ants from outside of the globe 21. The second plate 40 may also include a means for passage between the second plate 40 and subsequent, lower platforms 50 and 60. The ants may also pass between adjacent levels by way of the outer surface 15 of the cone 14. In this regard, the inner portion of selected platforms may include notches sized to accommodate the ants.

Another platform or plate 50 is positioned on the core 14 beneath and spaced apart from the second plate 40. This third plate 50 has a central support opening 51 and contains a food source for the ants. The food may comprise nectar, honey, sugar, fruit and the like and it may be positioned on the core 14 between the plates 40, 50, on the plate surface 52, or on a series of hooks 54 positioned at a predetermined spacing around the perimeter of the plate 50. The hooks 54 receive food portions 55 thereon and orient the food portions 55 in a manner such that feeding may be readily observed from the outside of the enclosure.

Lastly, a base platform or plate 60 is provided with a central opening 61 having a diameter which approximates the diameter of the base of the cone 14. This base plate 60 supports the enclosure 20 by way of engagement with an outer rim 62. The weight of the enclosure 20 maintains the base plate 60 in engagement with the core member rim 19. For applications wherein the feeding and observation apparatus is mounted on the ground, the base plate 60 supports the entire structure 10.

An additional platform or plate 70 may be provided exterior of the enclosure 20 at the entrance opening 22 thereof for the purpose of discouraging the ants from "swarming" over the globe and preventing observation of the inner platforms. Such a plate 70 includes an annular ring 71 having a circular channel 73 defined between the central opening 72 and the outer perimeter 74 thereof. This channel 73 may be filled with a fluid which ants find undesirable, such as water, and effectively serves as a "moat" to discourage swarming.

Turning now to FIGS. 6–9, a second embodiment 100 of an insect observation and feeding apparatus is illustrated. Similar to the first embodiment, the apparatus 100 includes a central core member 102 disposed within a protective enclosure 104, shown as a hollow cylinder 106 and extending between opposing ends of the cylinder 106. As illustrated, the core member 102 includes a spiral-like strip 108 having two parallel side members 110 interconnected by a plurality of transverse members 112 which define a series of horizontal levels within the cylinder 106. The spirals of the strip 108 permit the core to present multiple portions of the core strip to an observer. The spiral strip 108 may be constructed of a plastic material having a textured outer surface which enhances adhesion between it and a food matter, such as honey, sugar, water, etc. Additionally, the spacing between adjacent levels may be such so as to support solid food.

Figure 9:
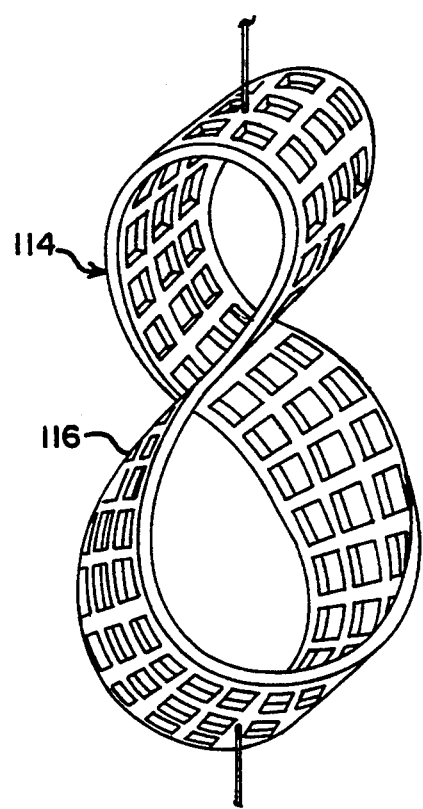
Figure 7:
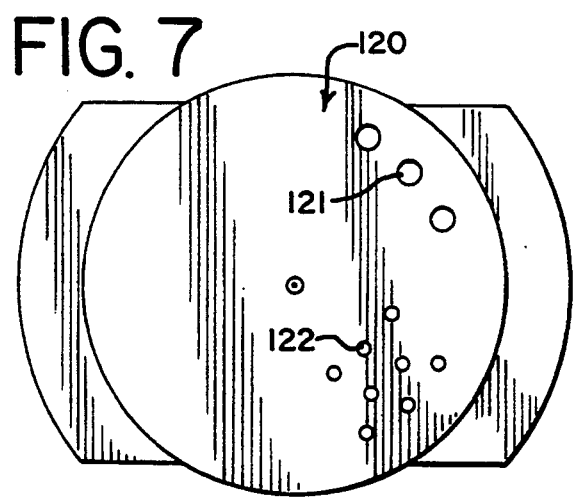
FIG. 7 is a sectional view taken along line 7—7 of FIG. 6 showing the entrance level.

An alternative food supporting core member 114 is illustrated in FIG. 9 as having the form of a Moebius strip 116. This may be formed from a lattice material to provide support surfaces for food and to define a series of generally horizontal levels within the cylinder 106. The core member 114 extends between the opposite ends of the enclosure 104 and is attached to the apparatus end plates by way of a string, rod or the like. Yet another alternative food supporting core member may be a string 200 (shown in phantom in FIG. 6) which extends within and below the cylinder 106.

Access to the core member 102 and to the food positioned thereon is had by way of an opening platform or plate 120 (FIG. 7), typically disposed at the top of the apparatus 100. This platform 120 has a series of large and small diameter openings 121, 122, respectively, disposed therein in a preselected pattern, shown as a semi-circular pattern. A closure plate 124 is disposed adjacent to and above the opening platform 120 and may be rotated to close off one or more selected openings. A water barrier platform or plate 126 (FIG. 8) may be provided for attachment over the opening plate 120 around the periphery of the cylinder 106 and having a channel 127 therein to prevent the ants from swarming on the enclosure exterior as described above.

The individual components of the present invention lend themselves to being easily and simply produced by methods well known in the manufacturing arts, such as by injection molding for the enclosures and platforms or stamping where a metal is used for construction of the plates/platforms.

While the preferred embodiments of the invention have been shown and described, it will be obvious to those skilled in the art that changes or modifications may be made therein without departing from the true spirit and scope of the invention. For example, additional platforms and core members may be provided to increase the observation locations provided by the device.

What is claimed is:

1. A feeding and observation device for crawling insects, comprising:
a central core member, a protective enclosure member enclosing the core member, said core member having at least two distinct levels defined thereon, the levels being angularly disposed from the enclosure member, a portion of said core member being adapted to support a food source for the crawling insects, the device further including an access member having at least one opening therein which permits access of the crawling insects through said enclosure member and to said core member, said core member including a cone portion, said core member having at least two distinct levels including two platforms extending radially outwardly from said cone portion, one of said two platforms being adapted to hold a food source thereon and the other of said two platforms being an observation platform spaced apart from said food source platform, said device further including means for permitting a passage between said food source platform and said observation platform, the observation platform including a maze thereon.

2. The feeding and observation device of claim 1, wherein said enclosure member includes a hollow globe.

3. The feeding and observation device of claim 1, wherein said enclosure member includes a hollow cylinder.

4. The feeding and observation device of claim 1, wherein said at least two levels include a base member, said core member extending between the base member and said access member within said enclosure member, and the remainder of said at least two levels being disposed on said core member between said base and access members.

5. The feeding and observation device of claim 1, further including a rotatable closure member disposed adjacent to and in overlying relationship with said access member, whereby said access member opening can be selectively opened and closed.

6. The feeding and observation device of claim 1, further including a barrier ring member having a circular channel disposed proximate to said entrance openings and adapted to hold a fluid therein, the barrier ring member being disposed between said entrance openings and an exterior surface of said enclosure member.

7. An ant feeding and observation device, the device comprising an enclosure, a central core member disposed in the enclosure and extending between two opposing ends of said enclosure, said device including an assembly for selectively admitting ants into said enclosure and onto said central core member, said device further including one or more locations for supporting a food source for said ants, said core member including a base portion which contacts one end of said enclosure, and said core member further includes an access portion associated therewith which contacts the other end of said enclosure and which permits entry and egress of ants from the device, said core member including a cone, the cone having at least one annular ring member associated therewith and extending radially outwardly from said cone, said cone further including a second annular ring member extending radially outwardly from said cone, the second annular ring member being spaced apart from said one annular ring, said second annular ring member further including a maze portion adapted for passage of the ants therethrough.

8. The device of claim 7, wherein said enclosure includes a hollow cylinder.

9. The device of claim 7, wherein said enclosure includes hollow globe.

10. The device of claim 7, wherein said core member base portion supportingly engages said enclosure.

11. The device of claim 10, wherein said access portion engages a portion of an inner surface of said enclosure.

12. A crawling insect observation and feeding device comprising, in combination: a central body member, at least two annular plate elements engaging said central body member whereby said two plate elements are spaced apart from each other a preselected distance, one of said plate elements including means for supporting food thereon and the other of said plate elements including a labyrinth portion, and a ladder member located generally between said two plate elements, and a protective enclosure substantially enclosing said central body member and defining an insect observation and feeding portion of said central body member, the enclosure being supported on a radial projection of said central core member, said device further including an access assembly having a member for selectively allowing entrance and exit of crawling insects to and from said central body member enclosed in said enclosure.

* * * * *